US010362988B2

(12) United States Patent
Shoshani et al.

(10) Patent No.: US 10,362,988 B2
(45) **Date of Patent: *Jul. 30, 2019**

(54) FLOAT LOOP TEXTILE ELECTRODES AND METHODS OF KNITTING THEREOF

(71) Applicant: Healthwatch LTD., Herzeliya (IL)

(72) Inventors: Boaz Shoshani, Raanana (IL); Renen Ben David, Petah-Tikva (IL)

(73) Assignee: HEALTHWATCH LTD., Herzeliya (IL)

( * ) Notice: Subject to any disclaimer, the term of this patent is extended or adjusted under 35 U.S.C. 154(b) by 410 days.

This patent is subject to a terminal disclaimer.

(21) Appl. No.: 14/646,934

(22) PCT Filed: Nov. 23, 2013

(86) PCT No.: PCT/IL2013/050964
§ 371 (c)(1),
(2) Date: May 22, 2015

(87) PCT Pub. No.: WO2014/080404
PCT Pub. Date: May 30, 2014

(65) Prior Publication Data

US 2015/0297135 A1 Oct. 22, 2015

Related U.S. Application Data

(60) Provisional application No. 61/729,548, filed on Nov. 24, 2012, provisional application No. 61/763,961, filed on Feb. 13, 2013.

(51) Int. Cl.
*A61B 5/00* (2006.01)
*A61B 5/04* (2006.01)
(Continued)

(52) U.S. Cl.
CPC ........ *A61B 5/6804* (2013.01); *A41D 13/1281* (2013.01); *A61B 5/0408* (2013.01);
(Continued)

(58) Field of Classification Search
CPC ............. A41D 13/1281; A61B 5/0408; A61B 5/04085; A61B 5/6804; A61B 5/6805; A10B 2403/02431
(Continued)

(56) References Cited

U.S. PATENT DOCUMENTS 7,849,888 B2 12/2010 Karayianni et al.
8,032,199 B2 10/2011 Linti et al.
(Continued)

FOREIGN PATENT DOCUMENTS

WO 2012104826 A1 8/2012

OTHER PUBLICATIONS

International Search Report for PCT/IL2013/050964 dated Mar. 11, 2014.
(Continued)

*Primary Examiner* — Catherine M Voorhees
*Assistant Examiner* — Pamela M. Bays
(74) *Attorney, Agent, or Firm* — Troutman Sanders LLP

(57) ABSTRACT

A method for knitting a garment having a tubular form, including knitting at least one conductive textile electrode on a machine having N participating feeders and M needles. The method includes the steps of continuously knitting the tubular form with one or more flexible non-conductive yarns, and knitting the electrode integrally within the tubular form, using a conductive yarn, in addition to the non-conductive yarns. The conductive yarn is knitted in a float-loop form by knitting a stitch and skipping over y needles, as follows: repeatably knitting a line segment $L_k$, using feeder $F_i$ and starting at needle $D_1$; and knitting line segment
(Continued)

10 110 110 20 100 100 100 100 100 110 100 100 120 100

$L_{k+1}$, using the next feeder and start stitching the first float-loop at needle $D_{1+s}$ where $0<s<y$. The tubular form has a preconfigured 10 knitting density, wherein the electrode has a knitting density that is higher than the preconfigured knitting density of the tubular form.

23 Claims, 6 Drawing Sheets

(51) Int. Cl.

| | |
|---|---|
| ***A61B 5/0408*** | (2006.01) |
| ***D04B 1/14*** | (2006.01) |
| ***D04B 1/24*** | (2006.01) |
| ***A41D 13/12*** | (2006.01) |
| ***D04B 1/10*** | (2006.01) |
| ***D04B 1/16*** | (2006.01) |
| ***G06F 1/16*** | (2006.01) |

(52) U.S. Cl.
CPC ........ *A61B 5/04085* (2013.01); *A61B 5/6805* (2013.01); *D04B 1/102* (2013.01); *D04B 1/14* (2013.01); *D04B 1/16* (2013.01); *D04B 1/246* (2013.01); *G06F 1/163* (2013.01); *A61B 2562/0209* (2013.01); *A61B 2562/125* (2013.01); *D10B 2101/20* (2013.01); *D10B 2401/18* (2013.01); *D10B 2403/02431* (2013.01); *D10B 2509/00* (2013.01)

(58) Field of Classification Search
USPC ........................................................ 600/388
See application file for complete search history.

(56) References Cited

U.S. PATENT DOCUMENTS

| | | | | |
|---|---|---|---|---|
| 8,171,755 | B2 | 5/2012 | Jahn et al. | |
| 2002/0152775 | A1* | 10/2002 | Browder, Jr. .......... | D04B 35/04 66/121 |
| 2006/0281382 | A1* | 12/2006 | Karayianni .......... | D03D 1/0088 442/181 |
| 2008/0287022 | A1 | 11/2008 | Dhawan et al. | |
| 2009/0018428 | A1* | 1/2009 | Dias .................. | A41D 13/1281 600/388 |
| 2010/0208445 | A1 | 8/2010 | Asvadi et al. | |
| 2011/0259638 | A1 | 10/2011 | Sherrill et al. | |

OTHER PUBLICATIONS

Spencer, David J., Knitting Technology: A Comprehensive Handbook and Practical Guide, vol. 16 of Woodhead Publishing Series in Textiles, CRC Press, 2001, 9.4 The Float Stitch (p. 92), ISBN 1587161214.

Niir Board, The Complete Technology Book on Textile Spinning, Weaving, Finishing and Printing, National Institute of Industrial Re, 2009, p. 251—float loop, ISBN 8178330490.

* cited by examiner

Figure 2:
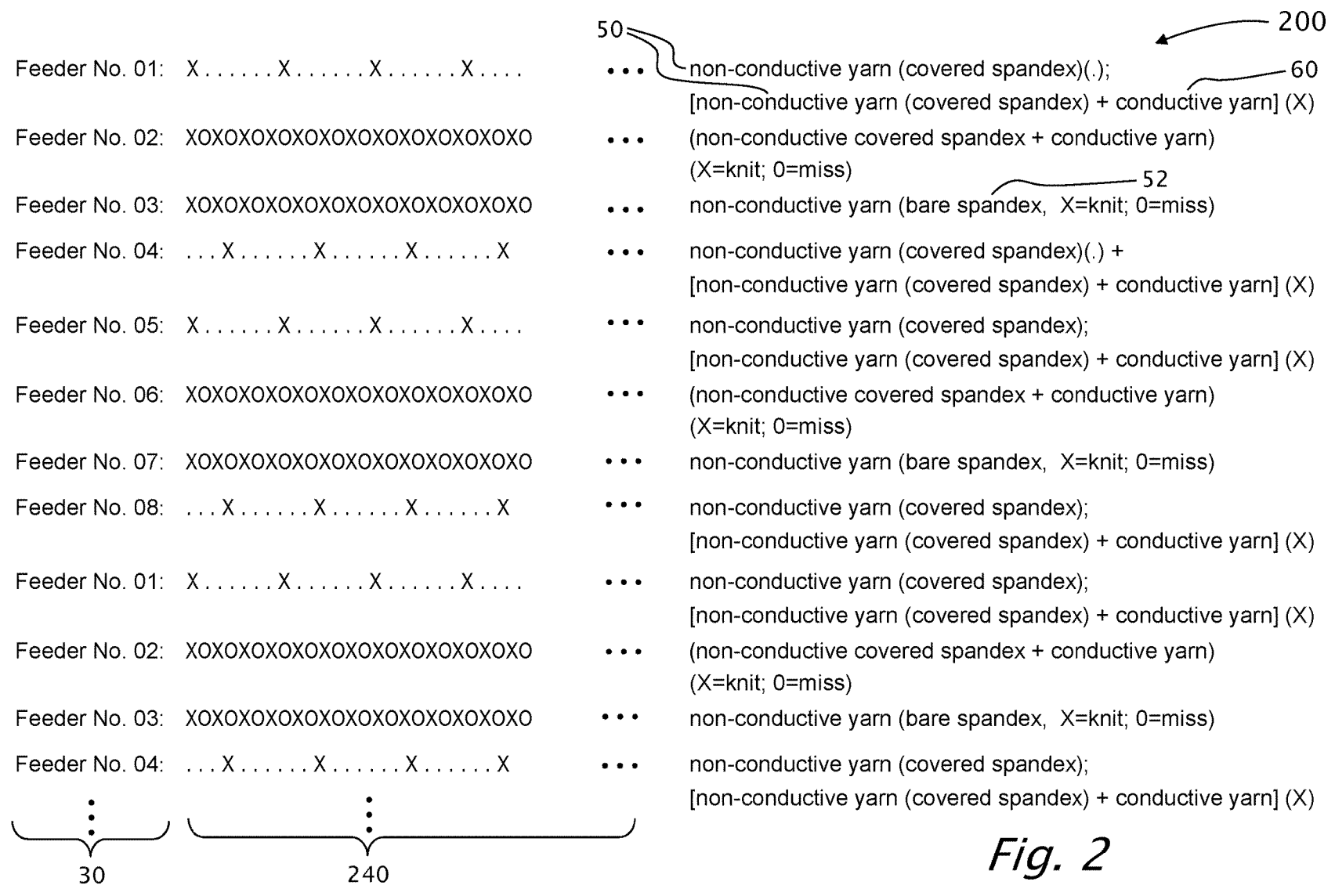

200

50

60

52

Feeder No. 01: X . . . . . . X . . . . . . X . . . . . . X . . . . • • • non-conductive yarn (covered spandex)(.); [non-conductive yarn (covered spandex) + conductive yarn] (X)

Feeder No. 02: XOXOXOXOXOXOXOXOXOXOXOXOXOXO • • • (non-conductive covered spandex + conductive yarn) (X=knit; 0=miss)

Feeder No. 03: XOXOXOXOXOXOXOXOXOXOXOXOXOXO • • • non-conductive yarn (bare spandex, X=knit; 0=miss)

Feeder No. 04: . . . X . . . . . . X . . . . . . X . . . . . . X • • • non-conductive yarn (covered spandex)(.) + [non-conductive yarn (covered spandex) + conductive yarn] (X)

Feeder No. 05: X . . . . . . X . . . . . . X . . . . . . X . . . . • • • non-conductive yarn (covered spandex); [non-conductive yarn (covered spandex) + conductive yarn] (X)

Feeder No. 06: XOXOXOXOXOXOXOXOXOXOXOXOXOXO • • • (non-conductive covered spandex + conductive yarn) (X=knit; 0=miss)

Feeder No. 07: XOXOXOXOXOXOXOXOXOXOXOXOXOXO • • • non-conductive yarn (bare spandex, X=knit; 0=miss)

Feeder No. 08: . . . X . . . . . . X . . . . . . X . . . . . . X • • • non-conductive yarn (covered spandex); [non-conductive yarn (covered spandex) + conductive yarn] (X)

Feeder No. 01: X . . . . . . X . . . . . . X . . . . . . X . . . . • • • non-conductive yarn (covered spandex); [non-conductive yarn (covered spandex) + conductive yarn] (X)

Feeder No. 02: XOXOXOXOXOXOXOXOXOXOXOXOXOXO • • • (non-conductive covered spandex + conductive yarn) (X=knit; 0=miss)

Feeder No. 03: XOXOXOXOXOXOXOXOXOXOXOXOXOXO • • • non-conductive yarn (bare spandex, X=knit; 0=miss)

Feeder No. 04: . . . X . . . . . . X . . . . . . X . . . . . . X • • • non-conductive yarn (covered spandex); [non-conductive yarn (covered spandex) + conductive yarn] (X)

FLOAT LOOP TEXTILE ELECTRODES AND METHODS OF KNITTING THEREOF

CROSS REFERENCE TO RELATED APPLICATIONS

This application claims the benefit under 35 USC 119(e) from U.S. provisional application 61/729,548 filed Nov. 24, 2012, and from U.S. provisional application 61/763,961 filed Feb. 13, 2013, the disclosures of which are included herein by reference.

FIELD OF THE INVENTION

The present invention relates to real-time health monitoring systems and more particularly, the present invention relates to knitted electrodes embedded into a knitted garment at preconfigured locations, wherein the electrodes and the garment form one piece. The electrodes are interconnected with a processor to form a health monitoring system.

The present invention provides novel dry textile contact electrodes, for measuring physiological parameters of a living being such as ECG signals and/or other vital signals such (EEG), electroencephalogram (EOG), electrooculogram and other medical measurements, wherein disposed adjacently to the skin of the monitored living being. The textile electrodes don not require any skin preparation, such as needed with wet electrode (usually gel) on hairy skin (usually shaving).

BACKGROUND OF THE INVENTION AND PRIOR ART

Monitoring systems for monitoring of physiological parameters of a living being are well known in prior art. For example, PCT/IL2010/000774, the disclosure of which is included herein by reference in its entirety, discloses a health monitoring system that continuously checks the wellbeing of a person (or any other living being) that, typically, is considered healthy (or with a known set of diseases), covering a significant range of health hazards that may cause a significant life style change/limitation, and provides an alert as early as possible—all this, with no significant limitation to the normal life style of the person bearing the system.

There exist other systems for monitoring heart rate, respiration and bio impedance, which can be used at home. Other systems, e.g. electroencephalographic (EEG) systems, electrocardiographic (ECG) or electromyographic (EMG) systems, are mainly adapted for clinical use, and typically use gel electrodes. The electrodes require a good skin contact to the monitored person. To make such electrodes more user friendly and easy to use, e.g. in a home environment, textile electrodes have been suggested. Such electrodes can be integrated into garments, for example, an undershirt.

Unlike conventional gel electrodes, which are directly applied to the living being's skin, using a conductive gel, textile electrodes are dry contact sensors adapted for use in measuring ECG signals and other vital signals such (EEG), electroencephalogram (EOG), electrooculogram and other medical measurements on the skin without any skin preparation, such as needed with wet electrodes, for example, shaving hairy skin.

Attempts have been made to tailor textile electrodes into a garment, in order to monitor health related physiological parameters of living beings. However such systems either record the signals for future, off-line analysis, or attempt to provide a health diagnosis. The off-line analysis may often prove to be too-late, and the health diagnosis is usually not accurate enough to trigger a definite intervention or instruction to the user.

The term "continuous monitoring", as used herein with conjunction with a health monitoring system, refers to a health monitoring system, facilitated to monitor a living being substantially continuous, day and night, when the monitored living being is awake or asleep, and active in substantially all common activities of such living being.

The term "seamless", as used herein with conjunction with a wearable device, refers to a device that when worn by an average person, wherein the device puts no significant limitation to the normal life style of that person and preferably not seen by anybody when used and not disturbingly felt by the user while wearing it. Furthermore, no activity is required from the monitored person in order for the system to provide a personal-alert when needed. It should be noted that people that pursue non-common life style, such as soldiers in combat zone or in combat training zone, or firefighters in training and action, or athletes in training or competition may utilize non-seamless devices. As the "seamless" characteristics refers also to the user's behavior, the wearable component is preferably an item that is normally worn (e.g., underwear) and not some additional item to be worn just for getting the alert.

The terms "underwear" or "garment", as used herein with conjunction with wearable clothing items, refers to seamless wearable clothing items that preferably, can be tightly worn adjacently to the body of a monitored living being, typically adjacently to the skin, including undershirts, sport shirts, brassiere, underpants, special hospital shirt, socks and the like. Typically, the terms "underwear" or "garment" refer to a clothing item that is worn adjacently to the external surface of the user's body, under external clothing or as the only clothing, in such way that the fact that there are sensors embedded therein, is not seen by any other person in regular daily behavior. An underwear item may also include a clothing item that is not underwear per se, but still is in direct and preferably tight contact with the skin, such as a T-shirt, sleeveless or sleeved shirts, sport-bra, tights, dancing-wear, and pants. The sensors, in such a case, can be embedded in such a way that are still unseen by external people to comply with the "seamless" requirement.

The terms "course" and "line segment", are used herein as related terms. The tubular form of the garment is knitted on a knitting machine, such as a Santoni knitting machine, where the tubular form is knitted in a spiral having substantially horizontal lines. A single spiral loop/circle us referred to herein as a course and a portion of a course is referred to as line segment.

The term "tightly" means that specific portions of the garment where there are electrodes or other sensors that require certain pressure on the body to obtain a satisfactory signal, are designed to be as tight as needed. However, all the other parts of the garment may be not as tight. Optionally, there is a provision to facilitate tightening or releasing certain portions of the garment, by built-in straps or other tightening means, so that the need for more or less tightness does not require the replacement of the whole garment.

The phrase "clinical level ECG", as used herein with conjunction with ECG measurements, refers to the professionally acceptable number of leads, sensitivity and specificity needed for a definite conclusion by most cardiology physicians to suspect a risky cardiac problem (for example, arrhythmia, myocardial ischemia, heart failure) that require immediate further investigation or intervention. Currently, it is at least a 12-leads ECG and preferably 15-lead ECG, coupled with a motion/posture compensation element, and a real-time processor with adequate algorithms.

Because ECG is a powerful and noninvasive tool that can provide high temporal resolution to directly reflect the dynamics of the heart activities, it has been widely used for medical diagnoses and CVD research. Conventional wet Ag/AgCl electrodes are generally and most frequently used to measure ECG signals. The conventional wet electrode characteristics have been widely studied and discussed in detail, including their applications. Indeed, ECG signal quality is excellent with a proper skin preparation (e.g. shaving hairy skin) and conductive gel usage.

However, skin preparation and the use of conductive gels are always required when using conventional wet electrodes, which is not user friendly and, typically, is therefore in clinical use only. These processes are employed to reduce skin-sensor interface impedance. In terms of the convenience of the ECG signal measurement process, these procedures usually create trouble for users, especially in daily life applications for long-term monitoring. In particular, the use of conductive gels inevitably leaves residues on the chest. The gel may also leak out of the wet ECG electrodes, causing a short circuit between two electrodes in close proximity when too much gel is applied or the wet electrode is pushed down too hard on the chest. Moreover, the above-mentioned preparation procedures for wet electrodes also have some significant drawbacks, such as being time-consuming, uncomfortable, and painful for participants because the skin preparation usually involves outer skin layer abrasion.

Repeated skin preparations and gel applications may also induce allergic reactions or infections. The ECG signal quality may degrade over extensive time periods as the skin regenerates and/or the conductive gel dries. Some issues also arise when measuring location that is covered with hair. This procedure leads to insufficient skin-electrode contact area, especially for continues long-term studies. Dry textile electrodes may be used to acquire ECG signals without any skin preparation or the use of conductive gel.

There is therefore a need and it would be advantageous to have dry knitted electrodes coupled to operate with a system that facilitates measuring health related physiological parameters of a living being, such as clinical level electrocardiogram (ECG) and enables real-time analyze the sensed data, while the living being is at rest or in motion. Furthermore, textile electrodes may provide comfort of use, facilitating continuously and seamlessly monitor a person, providing physiological parameters of that person.

BRIEF SUMMARY OF THE INVENTION

To be able to conduct continuous long term monitoring, a textile substrate is used to develop dry textile electrodes for sensing physiological parameters of a living being such as ECG signals. The dry textile electrodes include multiple float loops formed on the skin-side surface of the electrodes, facilitating acquisition of heart ECG signals having clinical quality. The float loops are used to penetrate the outer skin surface hairy layers to acquire the signals. The characteristics of this kind of textile dry electrode have been successfully compared with equivalent circuits of wet electrodes. Hence, the user friendly dry textile electrodes, having multiple float loops, can be used to acquire ECG signals without any skin preparation or using conductive gel.

For multi-lead ECG measurements, multiple textile are embedded into a garment by integrally knitting the textile electrodes with the garment (for example, by using a Santoni knitting machine), wherein the dry textile electrodes are coupled to operate with a multi-lead ECG measuring device, configured to detect continuous cardiac electrical activity. The multi-lead ECG measuring device is in operational communication flow with the textile electrodes to receive that sensed data.

The textile electrodes are typically made of washable conductive yarn. The exact bodily placement of each textile electrode is part of a preconfigured design of each type of monitoring-garment. For example, with no limitations, the bodily placement of each textile electrode is adapted to cover ECG skin measuring locations on the body.

The textile electrodes may vary in size and shape, being part of an innovative design, and are knitted in an innovative float loop formation or cut-loop formation (any third dimension formation) to improve the contact of the textile electrodes with the body. The textile electrodes enable good signals reading including on hairy type skins with no need to wet or remove the hair from the respective skin location, as done when using gel type electrodes.

According to teachings of the present invention, there is provided a method for knitting a garment having a tubular form being knitted with a base-yarn, including knitting at least one conductive textile electrode, using a knitting machine, such as a Santoni knitting machine, having N participating feeders and M needles. The base-yarn does not participate in the knitting of the conductive textile electrode. The method includes the steps of continuously knitting the tubular form with one or more flexible non-conductive yarns, and knitting the at least one textile electrode integrally within the tubular form, using a conductive yarn, in addition to the non-conductive yarns. The conductive yarn is knitted in a float-loop form by knitting a stitch and skipping over y needles, as follows:

i) knitting a line segment $L_k$, using feeder $F_i$ and start stitching with needle $D_j$, wherein typically, j=1;

ii) knitting line segment $L_{k+1}$, using feeder $F_{i+1}$ and start stitching the first float-loop with needle $D_j$+s, where 0<s<y; and iii) repeat steps (i) and (ii) for a preconfigured number of line segments, wherein each line segment has a preconfigured length.

Optionally, the knitting of the at least one textile electrode further includes the step of knitting one or more additional line segments of non-conductive yarn, in between the consecutive line segments containing the float-loop forms. The one or more additional line segments are knitted in a knitting scheme selected from the group of knitting schemes including:

a) continuously knitting the one or more additional line segments with the one or more flexible non-conductive yarns; and b) knitting the one or more additional line segments with the one or more flexible non-conductive yarns in a knit&miss scheme.

The one or more additional line segments may include knitting also with a conductive yarn, in addition to the non-conductive yarn, wherein the knit&miss scheme may be selected from the group of knitting schemes including:

a) knit-one&miss-one knitting pattern;

b) knit-two&miss-one knitting pattern; and c) knit-one&miss-two knitting pattern.

The tubular form has a preconfigured knitting density. Preferably, the at least one textile electrode has a knitting density that is higher than the preconfigured knitting density of the tubular form.

Optionally, a preconfigured region of the tubular form, disposed around and adjacently to the at least one textile electrode, is knitted with higher knitting density than the preconfigured knitting density of the tubular form.

Optionally, one or more preconfigured knitted regions have a knitting density that is higher than the preconfigured knitting density of the tubular form.

BRIEF DESCRIPTION OF THE DRAWINGS

The present invention will become fully understood from the detailed description given herein below and the accompanying drawings, which are given by way of illustration and example only and thus not limitative of the present invention, and wherein:

FIG. 2 outlines an example knitting scheme of a conductive electrode designed for a Santoni type knitting machine, according to embodiments of the present invention, wherein the float loop is made of a conductive yarn made of Nylon covered with silver or stainless steel, knitted together with covered Spandex and bare spandex.

DETAILED DESCRIPTION OF THE INVENTION

Figure 1B:
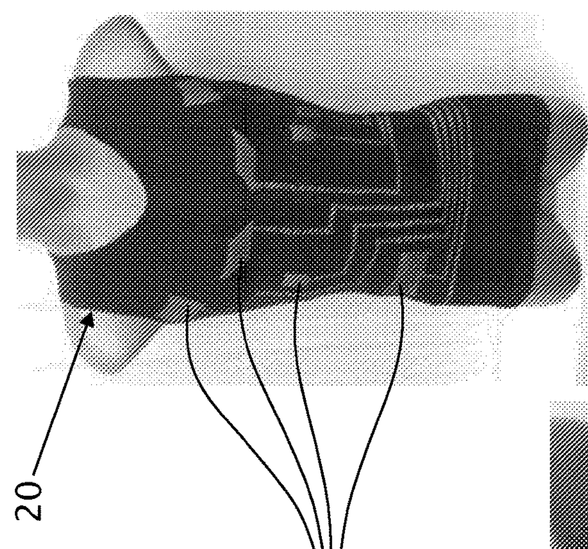
FIG. 1*b* depicts a front view of an exemplary garment, wherein the textile electrodes are designed to measure a 15-lead ECG signal.

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided, so that this disclosure will be thorough and complete, and will fully convey the scope of the invention to those skilled in the art.

An embodiment is an example or implementation of the inventions. The various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "one embodiment", "an embodiment", "some embodiments" or "other embodiments" means that a particular feature, structure, or characteristic described in connection with the embodiments is included in at least one embodiments, but not necessarily all embodiments, of the inventions. It is understood that the phraseology and terminology employed herein is not to be construed as limiting and are for descriptive purpose only.

Methods of the present invention may be implemented by performing or completing manually, automatically, or a combination thereof, selected steps or tasks. The term "method" refers to manners, means, techniques and procedures for accomplishing a given task including, but not limited to, those manners, means, techniques and procedures either known to, or readily developed from known manners, means, techniques and procedures by practitioners of the art to which the invention belongs. The descriptions, examples, methods and materials presented in the claims and the specification are not to be construed as limiting but rather as illustrative only.

Meanings of technical and scientific terms used herein are to be commonly understood as to which the invention belongs, unless otherwise defined. The present invention can be implemented in the testing or practice with methods and materials equivalent or similar to those described herein.

The electrodes location and level of pressure of the electrode on the body, in particular for textile electrodes, is critical for measuring electrocardiogram (ECG), electroencephalogram (EEG), electrooculogram (EOG), and other medical parameters. The location, shape, and size of each of the electrodes are critical for good and efficient ECG, EEG, EOG, signals reading, while taking into account the efficiency of ECG reading signals, wearing comfort, correct size for men and women, knitting capabilities, etc.

Based on the anatomical location of each of the electrodes adapted to obtain, for example, a 15-lead ECG, the invention describes the development of knitted dry electrodes made of conductive yarns in certain float loop formation, which is knitted on seamless circular knitting machine type Santoni having the technical capability to design the right pressure of the knitted electrodes, and knit the different electrodes in preconfigured location on the garment, corresponding to target location on the monitored living being.

An intensive development work was done to check the right location, size and shape of the dry knitted electrodes in the knitted garment, taking into account the efficiency of ECG reading signals, wearing comfort, knitting capabilities, different raw materials, and fabric design limitations.

To sense physiological parameters of a living being, the dry textile conductive yarn is used to obtain contact with the skin of the living being at predetermined bodily locations. Float loops are used to obtain good inter-conductivity between the knitted lines, regardless of the skin being hairy or not. To obtain good pressure contact of the textile electrode with the skin the electrodes and the garment regions adjacent to the electrodes are knitted with varying knitting density.

Figure 1C:
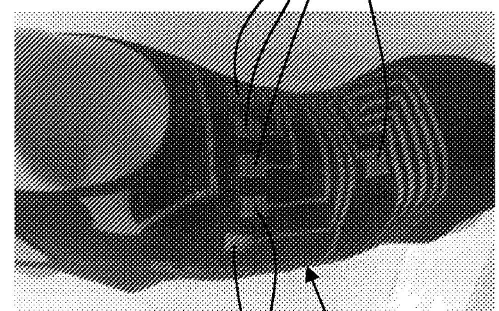
FIG. 1*c* depicts a side view of the garment shown in FIG. 1*b*.
Figure 1A:
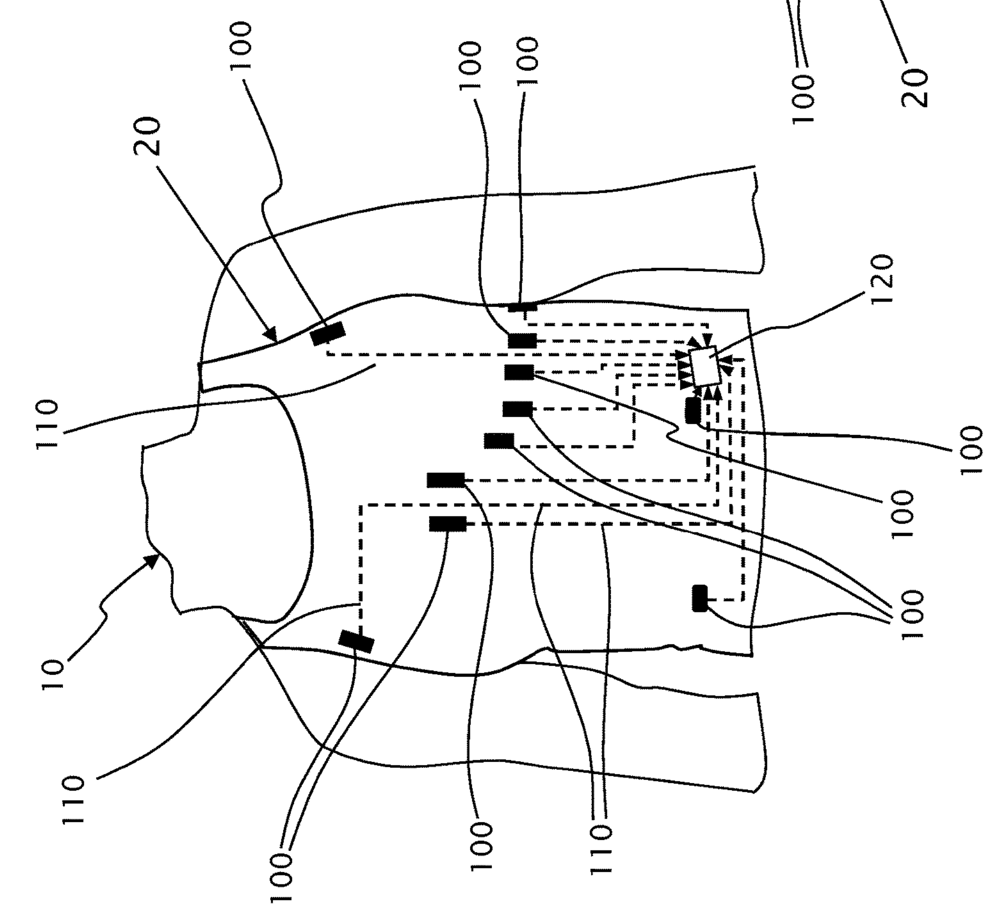
FIG. 1*a* is a schematic illustration of an exemplary garment, having a tubular form, wherein textile electrodes, according to embodiments of the present invention, are knitted therein.

FIG. 1*a* is a schematic illustration of an exemplary knitted smart garment 20, according to embodiments of the present invention, having knitted dry textile electrodes 100, wherein typically, textile electrodes 100 are interconnect with a processor 120 by conductive means 110. Knitted smart garment 20 has a tubular form, wherein dry textile electrodes 100 are knitted integrally therein. FIG. 1*b* depicts a front view of an exemplary garment 20, wherein the textile electrodes 100 are designed to measure a 15-lead ECG signal; and FIG. 1*c* depicts a side view of the garment shown in FIG. 1*b*.

Smart garment 20 is knitted, with no limitations, on a circular seamless knitting machine, such as a Santoni knitting machine. The fabric can be knitted, with no limitations, on a 24 gauge or 28 gauge machine (number of needles per inch) and in a wide range of diameters such as 17", 18" and 20", according to the final size and dimensions of the finished garment product.

In one example embodiment, with no limitations, the fabric is knitted with Nylon, bare Spandex and covered spandex. In another example embodiment, the fabric is typically knitted with a base-yarn such as Nylon and covered spandex. In one example embodiment, with no limitations, the conductive yarn used to knit the electrodes is Nylon coated with Silver by Xstatic.

It should be noted that such a garment can be knitted with any type of base-yarn including Nylon yarn textured or flat, selected types of Nylons, Polyester, Polypropylene, Acetate, manmade fibers, natural yarns like cotton, bamboo, wool, and blends of the mentioned raw materials. Selection of yarn is also based on fabric weight, body size for men and women, fabric weight and design required.

It is also to be mentioned that such a garment can be knitted on any given machine gauge or diameter based on the fabric weight, size, and design required.

The thickness (Den or Dtex) of the basic yarns to knit the garment and type of Spandex yarn used should be in line with the machine gauge and type of fabric requested. Spandex yarn is composed of synthetic fibers known for their exceptional elasticity.

The knitted electrodes are located in the selected areas on the fabric based on the desired ECG signals efficiency. Each electrode is connected to conductive lead wire (trace).

It should be noted that the term “ECG signals”, as used herein, refers the any physiological signals of the monitored living being, including signals for ECG analysis.

The knitted conductive leads are delivering the ECG signals sensed by the knitted electrodes to a specific area on the garment, were all the conductive leads are gathering to deliver the signals to the ECG processing device 120.

The knitted electrode 100 as described in FIG. 2 is knitted to form float loops made of the conductive yarns (for example, 70/2 Den by Xstatic), which are designed to float over the fabric surface in the number of needles as designed. The length of the float loop is determines by the number of needles the loop if floating over.

As described in this invention the length of the float loops, as well as the specific knitting density in the knitted electrode area, and in selected areas in the basic garment, is determined by the desired quality level of ECG signals.

In this invention the use of float loops in a shifted needle knitting scheme, together with unique digital knitting density control, enables achieving the following important advantages:

- Improve the pressure and the tightness of the electrodes to the body which is a critical parameter for good efficient ECG reading
- Obtaining good conductivity across knitting line segments.
- The electrodes are located well in the designated bodily position even when the body is in motion.
- The float loop electrodes can penetrate the hair on a hairy skin allowing reaching good ECG signals with no need to remove the hair as it is done today in regular ECG check.
- The float loop dry electrodes eliminating the use of gel or other wetting material used today to reach ECG signals.

The float-loop electrodes are knitted together in same knitting process of knitting the basic garment and coming out the machine as one single unit. FIG. 2 describe an example knitting method 200 of producing a float-loop electrode 100, according to embodiments of the present invention.

In this example embodiment, the conductive yarn is made of Nylon covered with silver or stainless steel, knitted on an 8-feeds Santoni type circular knitting machine (or machines with equivalent capabilities), together with the non-conductive yarns: covered Spandex 50 and bare spandex 52. In this example embodiment, the knitting scheme 240 uses 4 feeders 30 that are repeated for a preconfigured number of courses.

The base-yarn of the garment does not participate in the knitting of the conductive electrode. In the first course (Feeder No. 01), the float loops, formed from the conductive yarn 60 (such as Xstatic), float over 6 needles, as can be seen and appreciated by a person skilled in the art in FIG. 2, while the non-conductive covered spandex 50 is knitted continuously in the same knitted course.

In the second course (Feeder No. 02), the conductive yarn 60 and the non-conductive covered spandex 50 are knitted in the same pattern throughout the knitted course, wherein the yarns a alternately knitted in one needle and skip/miss the next needle, knit by the next needle and skip/miss the next needle, and so on and so forth (herein after referred to as a “knit-one&miss-one” knitting pattern).

In the third course (Feeder No. 03), a non-conductive yarn (such as a bare spandex) is knitted in a knit-one&miss-one knitting pattern.

In the fourth course (Feeder No. 04), as in the first course, float loops are formed from the conductive yarn 60, float over 6 needles, as can be seen in FIG. 2, while the non-conductive covered spandex 50 is knitted continuously in the same knitted course.

The above four courses are respectively repeated by feeders 5-8 and again by feeders 1-4 and so on and so forth.

According to aspects of the present invention, the length of the float loop (i.e. the no of needles the conductive yarn floats over) and the conductive yarn thickness (Den count), are determined by the desired level of penetration needed through a hairy chest and the quality level of the desired signals, such as ECG signals.

In variations of the present invention, the float repeat of the conductive yarn is changed according to the required level of knitting density.

It should also be noted that various thicknesses (Den count) may be used for conductive yarn 60 for knitting the float loops, as needed. The yarn thickness may affect the knitting efficiency.

In another embodiment of the present invention, in order to improve the ECG signals reading of an electrode, a different knitting scheme is used, wherein in this knitting scheme an increased number of float loops, per the same electrode area, are formed, providing an improved cohesion between an electrode and the skin of the monitored living being, and thereby obtaining better signals.

Figure 3:
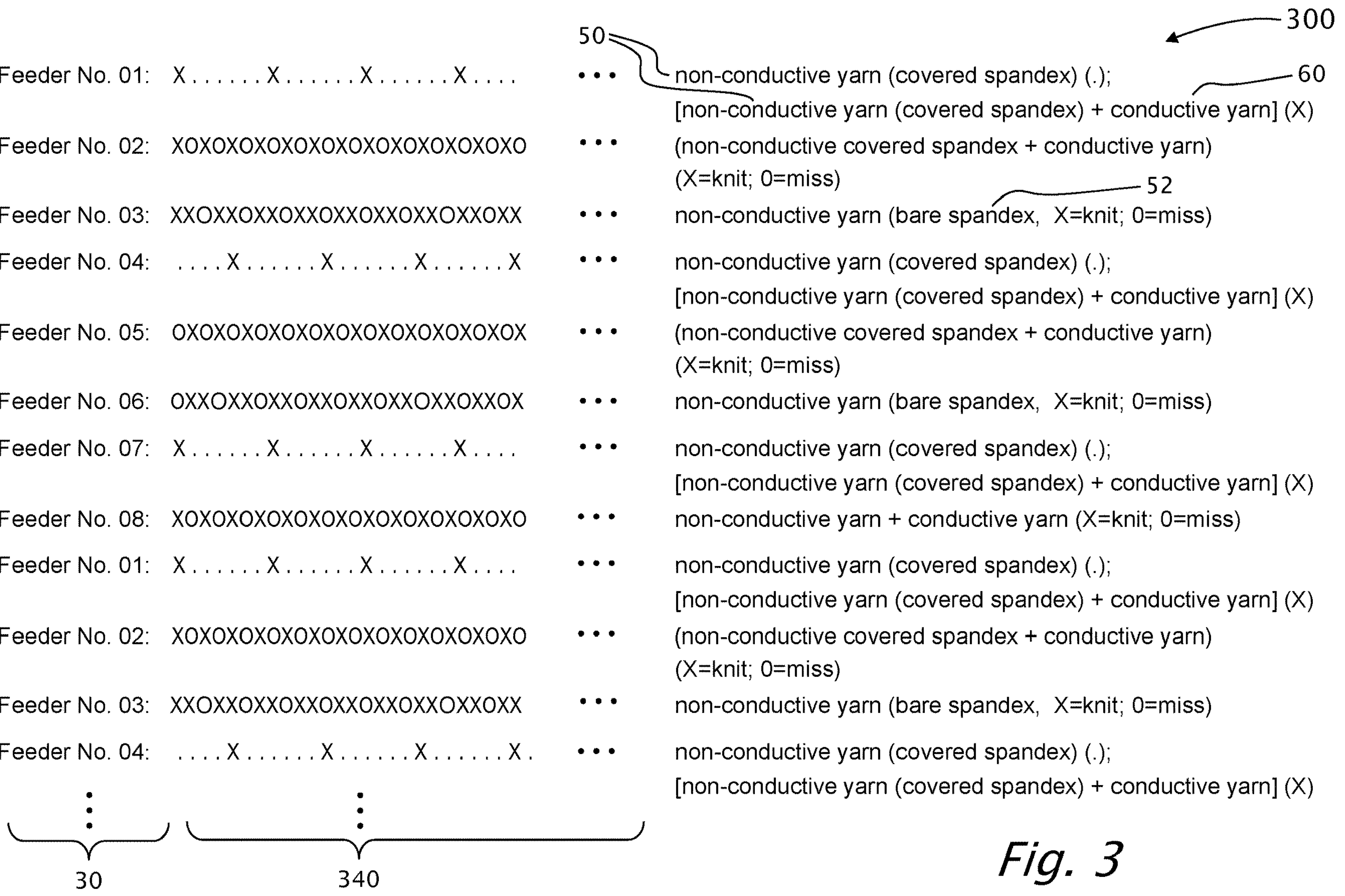
FIG. 3 outlines a knitting scheme being another example embodiment version of knitting a conductive float-loop electrode, based on a conductive yarn, a covered spandex yarn and a bare spandex yarn.

Reference is now made to FIG. 3, schematically illustrating another example knitting scheme 300 of a float-loop conductive electrode 100, designed for an 8 feeds Santoni type knitting machine, according to variations of the present invention.

In this embodiment, the knitting scheme 340 is based on an 8 feeds repeat with shifting positioning of the terry loops in feeders 1, 4 and 7, as shown in FIG. 3.

In the first, fourth and seventh courses (Feeders No. 01, 04 and 07), the float loops, formed from the conductive yarn 60 (such as Xstatic), float over 6 needles, as can be seen in FIG. 3, while the non-conductive covered spandex 50 is knitted continuously in the same knitted course. However, the float-loop stitch starting needle $D_j$ in Feeder No. 04 is shifted by s1 needles with respect to the float-loop stitch starting needle in Feeders No. 01 and 07. In the example shown in FIG. 3, s=4.

In the second, fifth and eighth courses (Feeders No. 02, 05 and 08), the conductive yarn 60 and the non-conductive covered spandex 50 are knitted in a knit-one&miss-one knitting pattern. However, the float-loop stitch starting needle $D_j$ in Feeder No. 05 is shifted by s2 needles with respect to the float-loop stitch starting needle $D_j$ in Feeders No. 02 and 08. In the example shown in FIG. 3, s2=1.

In the third and sixth courses (Feeders No. 03 and 06), a non-conductive yarn (such as a bare spandex) is knitted in the same pattern throughout the knitted course, wherein the yarns a alternately knitted in two adjacent needles and skip the next needle, knit by the next two adjacent needles and skip the next needle, and so on and so forth (herein after referred to as a "knit-two&miss-one" knitting pattern). However, the float-loop stitch starting needle $D_j$ in Feeder No. 06 is shifted by s3 needles with respect to the float-loop stitch starting needle $D_j$ in Feeder No. 03. In the example shown in FIG. 3, s3=1.

Figure 4:
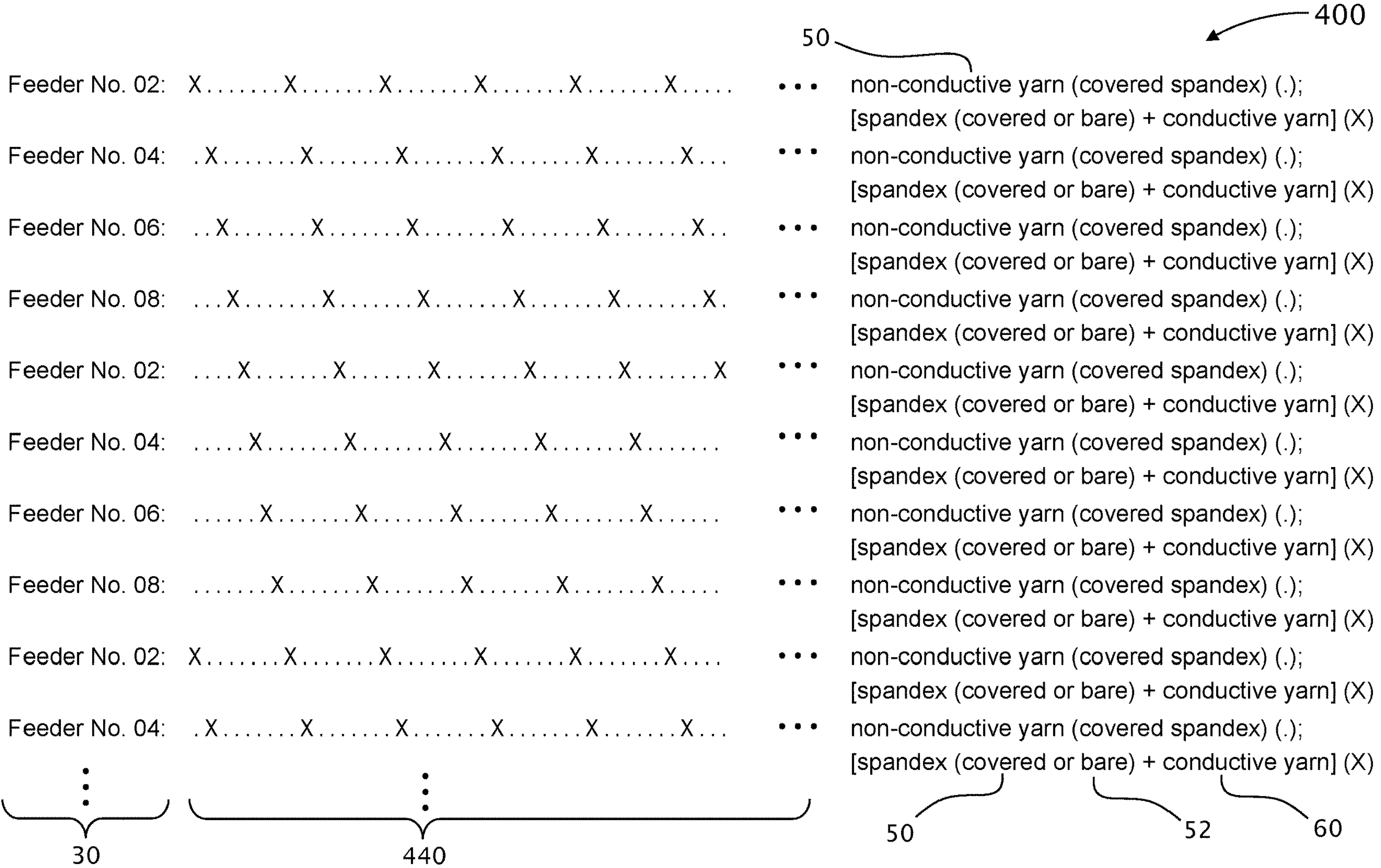
FIG. 4 outlines a knitting scheme being another improved version of conductive dry electrode which can be used in this embodiment. In this version the conductive electrode structure is based on conductive yarn, and covered spandex knitted in alternate float design to improve the knitting density and pressure of the electrode on the body.

Reference is now made to FIG. 4, schematically illustrating another example knitting scheme 400 of a float-loop conductive electrode 100, designed for a 4 (four) feeds system, but using in the example, with no limitations, an 8 feed Santoni type knitting machine, according to variations of the present invention.

In this embodiment, in all the knitting courses, the float loops that are formed from the conductive yarn 60 (such as Xstatic), that float over 7 needles, as can be seen and appreciated by a person skilled in the art in FIG. 4, while the non-conductive covered (or bared) spandex 50 is knitted continuously in the same knitted course. It should be noted that, in this embodiment, the base-yarn of the garment does not participate in the knitting of the conductive electrode.

In the example shown in FIG. 4, four out of eight available feeders are used: feeders 1, 3, 5 and 7 are not used while feeders 2, 4, 6 and 8 are used. The same knitting scheme 440 is used in all courses. However, the float-loop stitch starting needle $D_j$ in Feeder i+2 is shifted by s4 needles with respect to the float-loop stitch starting needle in Feeder i. In the example shown in FIG. 4, s4=1.

The present invention is not limited to the knitting parameters shown in the examples as illustrated in FIGS. 2-4 and corresponding description in the specifications. The examples as illustrated in FIGS. 2-4 exemplifies methods for knitting a garment 20 having a tubular form, including knitting at least one conductive textile electrode 100, using a knitting machine having N feeders and M needles.

In one embodiment the method includes continuously knitting a tubular form 20 with a flexible non-conductive yarn 50 and/or 52, knitting the at least one textile electrode 100 integrally within tubular form 20, using a conductive yarn 60, in addition to the non-conductive yarns. The conductive yarn 60 is knitted in a float-loop form by knitting a stitch and then skipping over y needles, as follows:

i) knitting a course k, being a line segment $L_k$, using feeder $F_i$ and starting at needle $D_j$, wherein the next float-loop starting stitch is at y needles away from the starting stitch needle of the previous float-loop;
ii) knitting line segment $L_{k+1}$, using the next participating feeder and starting stitching the first float-loop with needle $D_{j+s}$, where 0<s<y and typically, j=1; and
iii) repeat steps (i) and (ii) for a preconfigured length of the tubular form 20, i.e. a preconfigured number of knitting courses.

It should be noted that each line segment has a preconfigured length.

It should be further noted that a preconfigured number of feeders of the knitting machine participate in the knitting process of the garment.

It should be further noted that vertical conductive traces 110 can be knitted with various conductive yarn dtex and various number of filaments and on various gauge knitting machines.

In some embodiments, the method further includes knitting courses with a non-conductive yarn, such as bare spandex, in between consecutive courses containing the float-loops. The courses of a non-conductive yarn, and possibly together with a conductive yarn, may be knitted in a continuous or a knit&miss scheme, wherein the knit&miss may be in any combination, including knit one and miss one (knit-one&miss-one), knit two and skip one (knit-two&miss-one), knit one and skip two (knit-one&miss-two) and so on and so forth.

Figure 5:
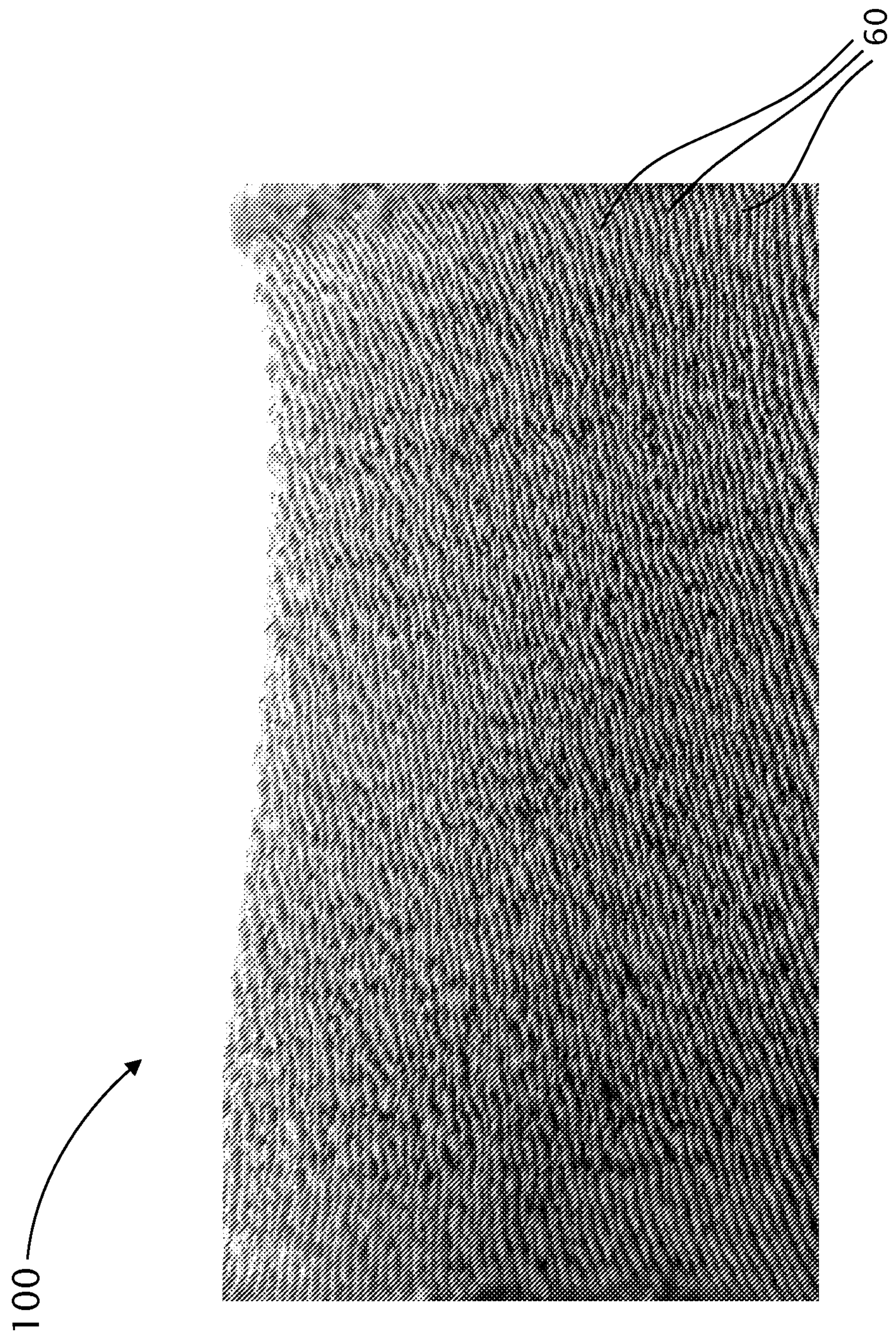
FIG. 5 depicts the "float loop" knitted electrode, formed via the knitting scheme shown in FIG. 4.

Reference is also made to FIG. 5, depicting the "float loop" knitted electrode, formed via the knitting scheme shown in FIG. 4.

To further enhance the quality of the signals read from the float-loop textile electrodes, a unique knitting density schemes are used for the electrode and for selected regions around the electrodes. Thus, facilitating better fitting and better contact of the electrodes onto the body skin, at respective target bodily locations.

Figure 6A:
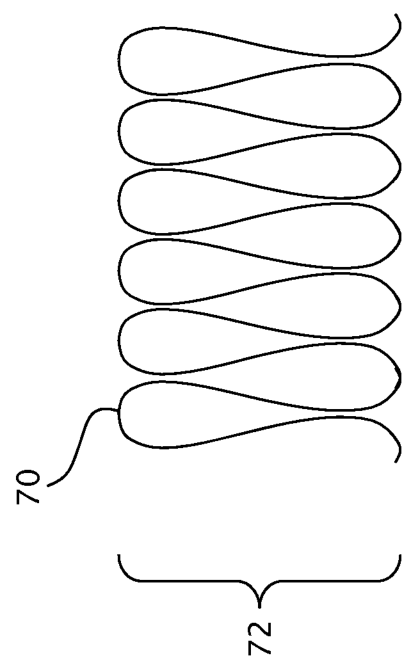
FIG. 6*a* schematically represents the mean terry loop knitting size, forming a mean knitting density value.
Figure 6B:
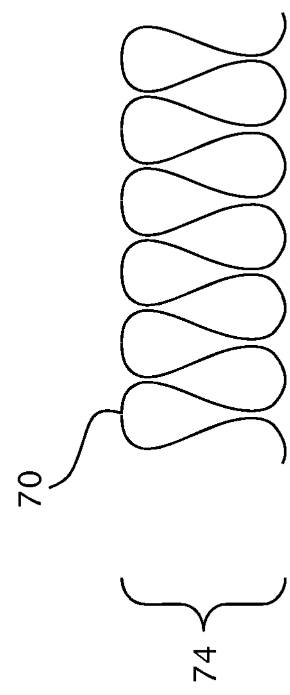
FIG. 6*b* schematically represents a terry loop knitting size that is smaller than the mean terry loop knitting size, shown in FIG. 6*a*.
Figure 6C:
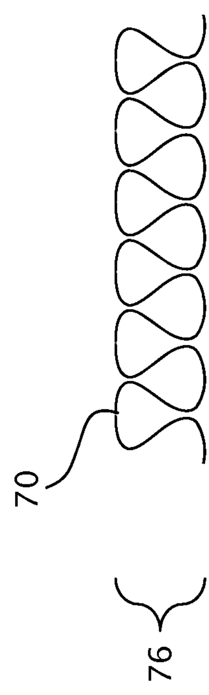
FIG. 6*c* schematically represents a terry loop knitting size that is smaller than the mean terry loop knitting size, shown in FIG. 6*b*.

The garment knitting method includes setting a mean terry loop knitting size for the tubular. In order to increase the knitting density one decreases the size of the terry loop and in order to decrease the knitting density one increases the size of the terry loop. Reference is now made to FIGS. 6*a*-6*c*, wherein the terry loop size, as shown schematically in FIG. 6*a* represents the mean terry loop knitting size (72) of a yarn 70, forming a mean knitting density value; FIG. 6*b* represents a terry loop knitting size (76) that is smaller than the mean terry loop knitting size (72), forming a higher knitting density than the means knitting density; and FIG. 6*c* represents a terry loop knitting size (76) that is smaller than the terry loop knitting size (74), as shown schematically in FIG. 6*b*, forming a lower knitting density than the means knitting density.

Typically, to increase the pressing force of the textile electrode against the body skin of the monitored living being, the textile electrode is knitted with a knitting density that is higher than the mean knitting density of the tubular form. Furthermore, to further increase the pressing force of the textile electrode against the body skin of the monitored living being, a preconfigured region of the tubular form, disposed around and adjacently to the textile electrode, is also knitted with higher knitting density than the mean knitting density of the tubular form.

The invention being thus described in terms of embodiments and examples, it will be obvious that the same may be varied in many ways. Such variations are not to be regarded as a departure from the spirit and scope of the invention, and all such modifications as would be obvious to one skilled in the art are intended to be included within the scope of the claims.

What is claimed is:

1. A knitted smart garment, the garment comprising:

a) a tubular form having variable elasticity, said tubular form having a multiplicity of knitted lines, wherein each said line is knitted with at least one non-conductive yarn by a circular knitting machine having a set of plurality of needles; and b) at least one conductive textile electrode for sensing an electrical vital signal, said at least one conductive textile electrode having:

i. a multiplicity of vertically-aligned adjacent knitted line segments, wherein each said line segment is knitted with a non-conductive yarn and a conductive yarn within a respective knitted line of said knitted lines; and ii. a skin-side face facing the skin and having a multiplicity of float loops, wherein said multiplicity of float loops is configured to electrically conduct said signal from a skin region;

wherein a first float loop of a given line segment of said multiplicity of vertically-aligned adjacent knitted line segments, begins in a given stitching position, and wherein the first float loop, in a previously knitted line segment that is adjacent to said given line segment, begins in a stitching position that is shifted by a preconfigured shifting position interval with respect to said given stitching position;

wherein said preconfigured shifting position is at least one needle position within the set of plurality of needles of the knitting machine; and wherein said at least one conductive textile electrode is adapted to be operatively connected with a processor.

2. The garment of claim 1, wherein said electrical vital signal is a clinical-level ECG signal.

3. The garment of claim 1, wherein said preconfigured shifting position is less than half of a number of skipped needle positions of each float loop of said multiplicity of float loops.

4. The garment of claim 1, wherein said preconfigured shifting position is adapted to create a suitable knitting density of said multiplicity of float loops, and wherein said suitable knitting density is adapted to prevent said multiplicity of float loops from folding substantially upon contact with said skin region, thereby enabling penetration of said multiplicity of float loops into said skin region to electrically conduct said signal from said skin region.

5. The garment of claim 1, wherein said preconfigured shifting position is adapted to create a suitable knitting density of said multiplicity of float loops, and wherein said suitable knitting density is adapted to provide good electrical conductivity across said multiplicity of vertically-aligned adjacent knitted line segments.

6. The garment of claim 1, wherein said tubular form has a designated knitting density, thereby providing a designated elasticity, and wherein said at least one conductive textile electrode has a knitting density that is substantially higher than said designated knitting density of said tubular form, thereby said at least one conductive textile electrode having a substantially lower elasticity than said tubular form.

7. The garment of claim 6, wherein a designated region of said tubular form, disposed around and adjacently to said at least one conductive textile electrode, is knitted with higher knitting density than said designated knitting density of said tubular form.

8. The garment of claim 1, wherein said at least one conductive textile electrode is knitted with a substantially lower density than regions adjacently surrounding said at least one conductive textile electrode, thereby said at least one conductive textile electrode having a substantially lower elasticity than said tubular form in said regions adjacently surrounding said at least one conductive textile electrode.

9. The garment of claim 1, wherein said tubular form has a designated knitting density, and wherein one or more designated regions have a knitting density that is higher than said designated knitting density of said tubular form, thereby providing said variable elasticity.

10. The garment of claim 1, wherein said skin region is either a non-hairy-skin region or a hairy-skin region.

11. A method for knitting a smart garment, the method comprising the steps of:

a) knitting a tubular form having variable elasticity, wherein said tubular form has a multiplicity of knitted lines, and wherein each said line is knitted with at least one non-conductive yarn by a circular knitting machine having a set of plurality of needles; and b) knitting at least one conductive textile electrode for sensing an electrical vital signal, wherein said at least one conductive textile electrode has:

i. a multiplicity of vertically-aligned adjacent knitted line segments, wherein each said line segment is knitted within said knitted lines with a non-conductive yarn and a conductive yarn; and ii. a skin-side face facing the skin and having a multiplicity of float loops, wherein said multiplicity of float loops is configured to electrically conduct said signal from a skin region;

wherein a first float loop of a given line segment of said multiplicity of vertically-aligned adjacent knitted line segments begins in a given stitching position, and wherein the first float loop, in a previously knitted line segment that is adjacent to said given line segment, begins in a stitching position that is shifted by a preconfigured shifting position interval with respect to said given stitching position;

wherein said preconfigured shifting position is at least one needle position within the set of plurality of needles on the knitting machine; and wherein said at least one conductive textile electrode is adapted to be operatively connected with a processor.

12. The method of claim 11, wherein said electrical vital signal is a clinical-level ECG signal.

13. The method of claim 11, wherein said preconfigured shifting position is less than half of a number of skipped needle positions of each float loop of said multiplicity of float loops.

14. The method of claim 11, wherein said preconfigured shifting position is adapted to create a suitable knitting density of said multiplicity of float loops, and wherein said suitable knitting density is adapted to prevent said multiplicity of float loops from folding substantially upon contact with said skin region, thereby enabling penetration of said multiplicity of float loops into said skin region to electrically conduct said signal from said skin region.

15. The method of claim 11, wherein said preconfigured shifting position is adapted to create a suitable knitting density of said multiplicity of float loops, and wherein said suitable knitting density is adapted to provide good electrical conductivity across said multiplicity of vertically-aligned adjacent knitted line segments.

16. The method of claim 11, wherein said knitting of said at least one conductive textile electrode further comprises the step of knitting at least one additional line segment of non-conductive yarn, in between consecutive vertically-aligned adjacent knitted line segments containing said multiplicity of float loops, wherein each said additional line segment is knitted in a knitting scheme selected from the group of knitting schemes comprising:

a) knitting each said additional line segment with an additional non-conductive yarn; and b) knitting each said additional line segment with an additional non-conductive yarn in a knit&miss scheme.

17. The method of claim 16, wherein each said additional line segment comprises knitting also with a conductive yarn, in addition to said additional non-conductive yarn.

18. The method of claim 16, wherein said knit&miss scheme is selected from the group of knitting schemes comprising:

a) knit-one&miss-one knitting pattern;

b) knit-two&miss-one knitting pattern; and c) knit-one&miss-two knitting pattern.

19. The method of claim 11, wherein said tubular form has a designated knitting density, thereby providing a designated elasticity, and wherein said at least one conductive textile electrode has a knitting density that is substantially higher than said designated knitting density of said tubular form, thereby said at least one conductive textile electrode having a substantially lower elasticity than said tubular form.

20. The method of claim 11, wherein a designated region of said tubular form, disposed around and adjacently to said at least one conductive textile electrode, is knitted with higher knitting density than said designated knitting density of said tubular form.

21. The method of claim 11, wherein said at least one conductive textile electrode is knitted with a substantially lower density than regions adjacently surrounding said at least one conductive textile electrode, thereby said at least one conductive textile electrode having a substantially lower elasticity than said tubular form in said regions adjacently surrounding said at least one conductive textile electrode.

22. The method of claim 11, wherein said tubular form has a designated knitting density, and wherein one or more designated knitted regions have a knitting density that is higher than said designated knitting density of said tubular form, thereby providing said variable elasticity.

23. The method of claim 11, wherein said skin region is either a non-hairy-skin region or a hairy-skin region.

* * * * *